US00PP09439P

United States Patent [19]

Moser

[11] Patent Number: Plant 9,439

[45] Date of Patent: Jan. 23, 1996

[54] AZALEA PLANT NAMED ATHENA

[75] Inventor: Frank C. Moser, Alva, Fla.

[73] Assignee: Yoder Brothers, Inc., Barberton, Ohio

[21] Appl. No.: 381,330

[22] Filed: Jan. 31, 1995

[51] Int. Cl.[6] ..... A01H 5/00

[52] U.S. Cl. ..... Plt./56

[58] Field of Search ..... Plt./55–57

[56] References Cited

PUBLICATIONS

Leach, D. G., "Appendix A, Complete Descriptive List of Rhododendron Hybrids" *Rhododendrons of the World,* 1961, Charles Schribner's Sons, N.Y. p. 431.

*Primary Examiner*—James R. Feyrer

*Attorney, Agent, or Firm*—Foley & Lardner

[57] ABSTRACT

An azalea plant named Anthena particularly characterized by its evergreen foliage, semi-double flower with slightly frilled margins, coral-pink flower color, ease of budding, uniform plant habit and flowering response in a year round controlled program, and by its excellent cooler tolerance and keeping quality.

1 Drawing Sheet

The present invention comprises a new and distinct cultivar of Azalea, a greenhouse forcing type, hereinafter referred to as Athena.

Athena, identified as Code 833 during the selection process, originated from a planned cross hybridization between two selected breeding lines in a controlled breeding program in Fort Myers, Fla. by the inventor Frank C. Moser.

The female, or seed parent, of Athena is the commercial cultivar Prize, a dark rose pink double hose-in-hose with vigorous upright habit disclosed in U.S. Plant Pat. No. 3,795. The male, or pollen parent, is a seedling known as Code 227, a proprietary breeding line.

Athena was discovered and selected as one flowering plant within the progeny of the stated cross by the inventor Frank C. Moser in October 1988, in Fory Myers, Fla.

The first asexual reproduction of Athena was accomplished when vegetative cuttings were taken from the initial selection in December 1988, in Fort Myers, Fla., by technicians working under formulations established and supervised by Frank C. Moser.

Horticultural examination of controlled flowerings of successive generations of plants derived from cuttings taken from the original selection has shown that the unique combination of characteristics as herein disclosed for Athena are fixed and retained through successive generations of asexual reproduction.

Athena has not been observed under all possible environmental conditions. The phenotype may vary significantly with variations in environment such as temperature, light intensity and daylength, without, however, any variance in the genotype.

The following observations, measurements and comparisons describe plants that were grown in Fort Myers, Fla. in a controlled greenhouse environment and following a commercial schedule.

The following traits have been repeatedly observed and are determined to be basic characteristics of Athena, which, in combination, distinguish this azalea as a new and distinct cultivar:

1. A coral-pink flower color (54D) fading to light pink (56B) at old age.

2. Semi-double flowers with a slightly frilled petal margin. The flowers range in size from 5.5 to 8.0 cm in diameter, with 7.0 cm the average size.

3. Compact, uniform and symmetrical plant habit.

4. Fast, uniform response in a year-round controlled flowering program, forcing in 26 days on average.

5. Excellent longevity in a simulated home environment, with flowers lasting up to 32 days.

6. Excellent foliage retention and no flower bud damage when cooled for six (6) weeks with no lighting at 38° F.

The accompanying color photograph shows in perspective view the unique features of the new cultivar, with colors being as true as possible with color illustrations of this type.

Of the commercial cultivars known to the inventor, the most similar in comparison to Athena is the unpatented cultivar Gloria. Athena is generally similar to Gloria in having coral-pink flower color, but the colors of the respective cultivar are not precisely the same.

Athena differs from Gloria in that the flowers of Athena do not have as distinct a flower blotch or white petal margin. The flower form of Athena is more double and the flower margins are frillier than those of Gloria. The growth habit of Athena is more compact than that of Gloria. In groups of plants grown in Fort Myers, Fla., Athena last up to two weeks longer in keeping quality trials and exhibits a greater resistance to cylindrocladium root and stem rot than does Gloria.

In the following description color references are made to The Royal Horticultural Society Colour Chart. The color values were determined on Jul. 6, 1994. All readings were taken in an office under cool white fluorescent lights, facing a west window between the hours of 10:00 a.m. and 2:00 p.m.

Classification:

*Botanical.*—*Rhododendron hybrida,* evergreen type.

*Commercial.*—Florist forcing pot azalea, cv. Athena.

INFLORESCENCE

Flower (general):

*Size.*—5.5 to 8.0 cm.

*Born.*—Terminal cluster, usually three (3) per bud, ranging from two to four (2–4). Occasionally more than one (1) bud per stem.

*Form.*—Semi-double, funnel-form.

*Blooming habit.*—Once, profusely. Buds easily and uniformly in a year-round flowering program. The majority of terminal buds break color within one (1) week of the first. Flowering begins approximately 26 days after the start of forcing.

*Fragrance.*—None.

Corolla (petals):

*Texture.*—Soft.

*Substance.*—Heavy.

*Shape.*—Rounded with slightly frilled margin.

*Color (fully open).*—Generally 54D, coral-pink. Upper surface: Edge: 54D. Center: 54C. Base: 50C. Lower surface: 39B. Blotch: 57C, very diffused.

Bud:

*Size.*—Medium.

*Shape.*—Conoidal.

*Color.*—52D.

*Bud sheath.*—Light green with light brown hairs.

Calyx:

*Form.*—Acute.

*Color.*—143A.

Peduncle:

*Length.*—1.5–3.0 cm.

*Strength.*—Strong.

*Aspect.*—Pubescent.

Reproductive organs:

*Androecium (stamens).*— Number: Zero to five (0–5). Many are fully or partially transformed into petals. Anthers: 11B. Filaments: Length: 1.0–2.0 cm. Color: 36D.

*Gynoecium (pistil).*— Stigma: 149A. Style: Length: 2.5–3.5 cm. Color: 55C. Ovary: Pubescent.

PLANT CHARACTERISTICS

Foliage:

*Height.*—Evergreen.

*Arrangement.*—Alternate.

*Shape.*—Elliptic.

*Size.*—Length: 3.0–6.5 cm. Width: 1.3–2.5 cm.

*Margin.*—Entire.

*Color.*—Immature: Upper surface: 146A. Lower surface: 146C. Mature: Upper surface: 147A. Lower surface: 146A.

*Texture.*—Leathery.

*Tomentum.*—Present on upper surface. Insignificant.

Stems:

*Color.*—Immature: 145A. Mature: 166B. Tomentum: 166B.

Plant habit: Compact, semi-upright bush which is uniform and symmetrical in a six-inch (6") pot when pinched three (3) times. Total crop time to the dormant budded stage is 40–42 weeks to produce a plant approximately 30 cm in diameter and having a total height of 30–36 cm. Internode lengths vary widely from 2–20 mm on the same stem.

Branching habit: Free branching, producing three to four (3–4) breaks when a vegetative cutting is pinched.

Rooting: Roots easily in eight to ten (8–10) weeks with 75° F. soil temperature.

Budding ease: Plants produce flower buds easily and uniformly year round with the use of commercially available plant growth regulators. Natural season response has not been ascertained.

Cooler tolerance: Plants placed in a cooler as a means of breaking dormancy perform very well. Athena is tolerant of six (6) weeks in an unlighted cooler without excessive bud damage or foliage loss.

Blooming: Plants reach the stage of 12 buds showing color in 26 days on average after the cooling treatment. This varies from 18–40 days depending upon time of year. Athena flowers uniformly and profusely across the plant.

Shelf life: When plants are moved to an office or home environment at the stage of eight (8) open flowers, they maintain an attractive appearance for 32 days on average.

It is claimed:

1. A new and distinct cultivar of azalea named Athena, as described and illustrated.

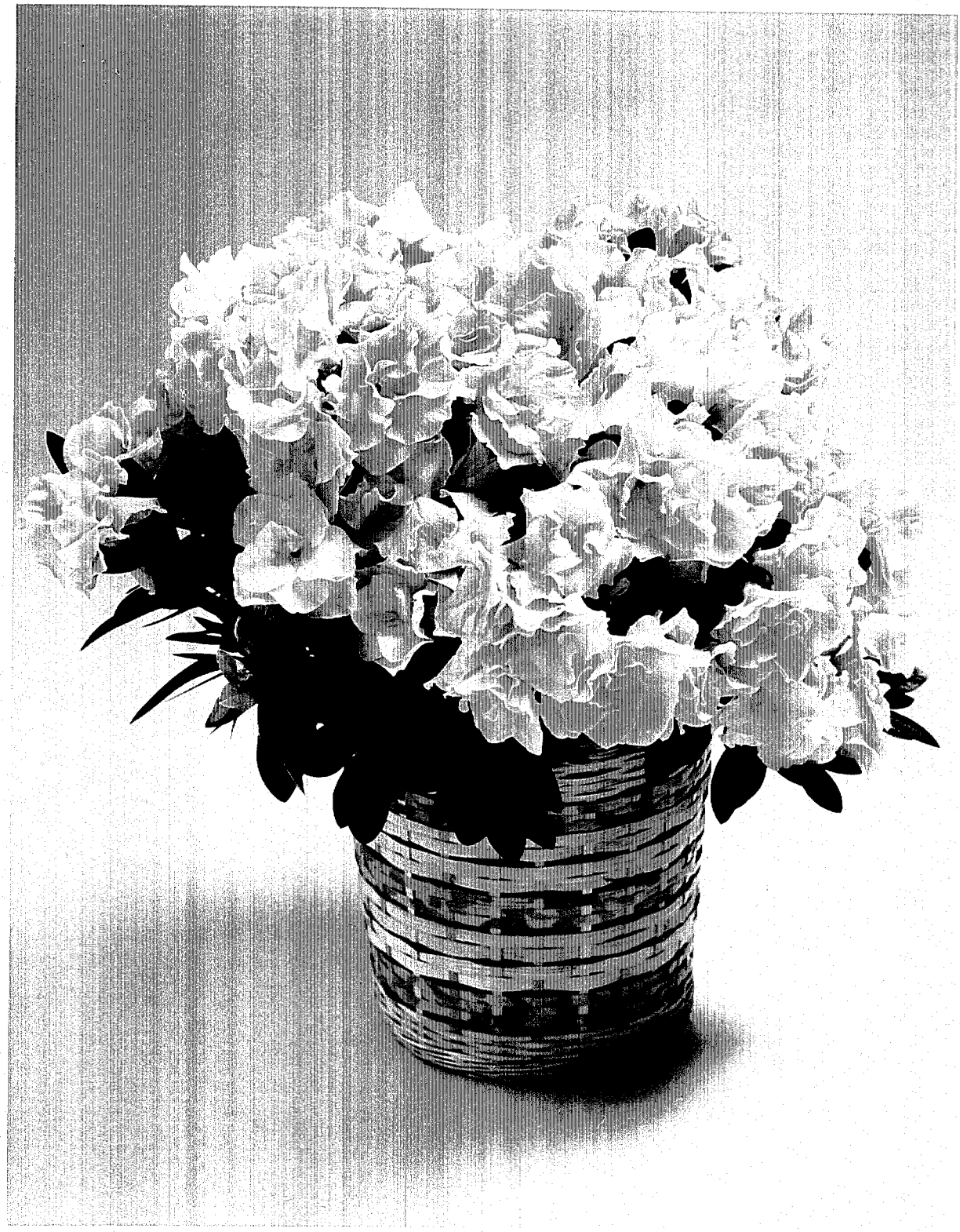

* * * * *